United States Patent
Berndt et al.

(10) Patent No.: US 6,812,357 B2
(45) Date of Patent: Nov. 2, 2004

(54) METHOD FOR PRODUCING EPOXIDES BY OXIDIZING OLEFINS

(75) Inventors: Torsten Berndt, Leinefelde (DE); Olaf Boege, Schkeuditz OT Glesien (DE); Jost Heintzenberg, Leipzig (DE)

(73) Assignee: Institute Fuer Troposphaerenforschung E.V., Leipzig (DE)

( * ) Notice: Subject to any disclaimer, the term of this patent is extended or adjusted under 35 U.S.C. 154(b) by 0 days.

(21) Appl. No.: 10/363,170

(22) PCT Filed: Sep. 5, 2001

(86) PCT No.: PCT/EP01/10231
§ 371 (c)(1),
(2), (4) Date: Sep. 5, 2003

(87) PCT Pub. No.: WO02/20502
PCT Pub. Date: Mar. 14, 2002

(65) Prior Publication Data
US 2004/0054202 A1 Mar. 18, 2004

(30) Foreign Application Priority Data
Sep. 5, 2000 (DE) ......................................... 100 44 538

(51) Int. Cl.⁷ ............................................. C07D 301/02
(52) U.S. Cl. ....................................... 549/518; 549/523
(58) Field of Search ................................. 549/578, 523

(56) References Cited

U.S. PATENT DOCUMENTS 5,625,084 A   4/1997   Pitchai et al.
5,686,380 A   11/1997  Pitchai et al.
5,760,254 A   6/1998   Grey
5,763,630 A   6/1998   Kahn et al.
6,083,870 A   7/2000   Kahn et al.
6,303,800 B1  10/2001  Dingerdissen et al.

FOREIGN PATENT DOCUMENTS

| DE | 12 19 014 | | 7/1959 |
| WO | WO 97/28142 | * | 8/1997 |
| WO | WO 97 28142 | | 8/1997 |
| WO | WO 97 34693 | | 9/1997 |
| WO | WO 97/34693 | * | 9/1997 |
| WO | WO 99 29679 | | 6/1999 |

OTHER PUBLICATIONS

R. N. Schindler, "Mechanistic and Kinetic Studies of Selected Oxidation Steps of Tropospheric Interest", *Transport. Chem. Transform. Pollutants. Troposphere*, 1997, vol. 3, pp. 208–213.

* cited by examiner

*Primary Examiner*—Amelia A. Owens
(74) *Attorney, Agent, or Firm*—Millen, White, Zelano & Branigan, P.C.

(57) ABSTRACT

The invention relates to a new method for producing epoxides by oxidizing olefins in a homogeneous gas phase reaction, wherein ozone and $NO_2$ and/or NO are reacted with the desired olefin under mild reaction conditions and without a catalyst. The inventive method can be carried out as a continuous, one-step method in a reactor according to FIG. 1, and requires very little technical input. Monoolefins having 2 to 16 carbon atoms and diolefins having 4 to 16 carbon atoms can be epoxidized.

20 Claims, 1 Drawing Sheet

METHOD FOR PRODUCING EPOXIDES BY OXIDIZING OLEFINS

DESCRIPTION

The invention relates to a new method of producing epoxides via oxidation of olefins in a homogeneous gas-phase reaction by reacting ozone and $NO_2$ and/or NO with the desired olefin under mild reaction conditions without using a catalyst. The method of the invention can be carried out as a continuous one-step method in a reactor according to FIG. 1, and requires very little technical input. Monoolefins having 2 to 16 carbon atoms and diolefins having 4 to 16 carbon atoms can be epoxidized.

Epoxides are important intermediates in the chemical industry and are mainly used in the production of olefin glycols or di-, poly- or oligomers thereof which mostly are processed further to form polyurethanes. In particular, propylene oxide and ethylene oxide each are required in amounts of about 5 million tons per year.

Epoxides can be produced from olefins by the chlorohydrin process, by indirect oxidation processes using peroxide reagents, and by catalytic or non-catalytic direct oxidation processes. The oxidations can be carried out in liquid phase or in gaseous phase. Oxidations in liquid phase, which can be carried out either as homogeneous or heterogeneous oxidations, are associated with difficult separation processes and complicated technologies. Direct olefin oxidation processes in the gaseous involve relatively long residence times and frequently furnish excessively low conversion and/or excessively low selectivity with respect to the epoxide.

Thus, for example, DE 197 54 303 A1 describes a method of producing propylene oxide from propylene in a homogeneous gas-phase reaction. While this method has a selectivity with respect to propylene oxide of >60%, the propylene conversion is relatively low, being 13% and 15%, respectively. In addition, the method is technically complex and costly because the reactor's interior according to this invention is lined with an inert material, particularly with noble metals.

It was the object of the present invention to provide a method of producing epoxides by oxidizing olefins, which method requires low technical input, is favorable in cost, and ensures both high selectivity with respect to the epoxide produced and high conversion of the olefin employed.

It was found that epoxides can be produced via oxidation of olefins in a homogeneous, continuous gas-phase process with good yields and good selectivities with respect to the epoxide produced, by mixing ozone and $NO_2$ and/or NO, optionally using a carrier gas, passing the resultant gas mixture into a conventional flow reactor, and reacting the corresponding olefin fed with the carrier gas under mild reaction conditions. According to the invention, a pressure of not more than 0.1–1000 mbar, preferably 1–500 mbar, and more preferably 1–200 mbar, is required. The temperature required is 50–350° C., preferably 100–300° C., and more preferably 140–240° C. No catalyst is required in the method according to the invention. The residence time in the reaction zone is from 0.1 ms to a few seconds at maximum, and is preferably between 0.1 and 300 ms.

Oxygen, as well as inert gases such as helium, argon, nitrogen or mixtures thereof with oxygen can be used as carrier gases.

According to the invention, ozone and $NO_2$ are employed at a ratio of <0.5. Ozone and NO are preferably employed at a ratio of <1.5.

In a preferred embodiment of the invention, ozone is supplied as an ozone/oxygen mixture, preferably 1–15 vol.-% ozone in oxygen, and more preferably 5–10 vol.-% ozone in oxygen.

The method of the invention is carried out in a conventional flow reactor supplied with said gas mixture of ozone and $NO_2$ and/or NO and optional carrier gas. Preferably, the method is performed in a reactor according to FIG. 1.

Figure 1:
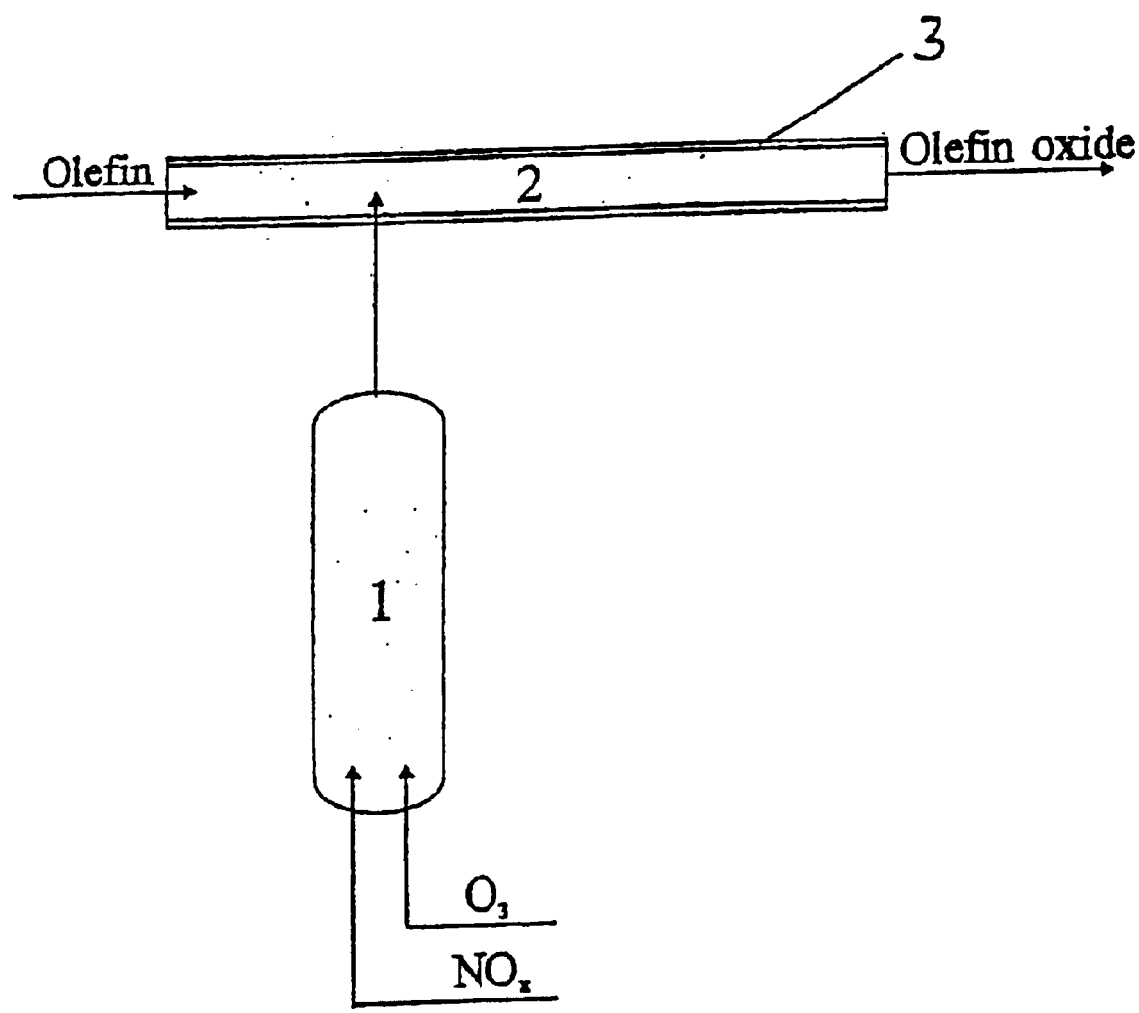
In FIG. 1.

1 Mixing chamber
2 Flow reactor
3 Heatable exterior jacket

In the mixing chamber 1, which is connected with the flow reactor 2, ozone and $NO_2$ and/or NO, optionally with carrier gas, are mixed together. Preferably, this can be done at room temperature. The flow reactor is made of conventional materials stable under the pressure conditions used, and coating thereof with inert materials is not required. The results according to the invention are also achieved in a flow reactor made of normal standard steel. Optionally, the flow reactor can be connected to a GC-MS analyzer and/or a gas flow cell with an FT-IR spectrometer, depending on the intended analysis of the reaction gas.

The method of the invention is universally applicable in that the method allows for epoxidation of monoolefins having 2 to 16 carbon atoms, preferably up to 5 carbon atoms, most preferably propylene and $C_4$ olefins, and of diolefins having 4 to 16 carbon atoms. The reactor according to FIG. 1 can be used with all of the above-mentioned olefins.

Thus, according to the invention, a continuous one-step method is provided, which requires very little technical input, operates under mild reaction conditions, does not require a catalyst, and exhibits very short residence time in the reaction zone, i.e., high throughput. The selectivity with respect to the epoxide produced is at least 68%, and, in addition, high conversion of at least about 50% is achieved.

With reference to the examples, the invention will be illustrated in more detail below.

EXAMPLES

Example 1

Oxidation of Propylene to Form Propylene Oxide

A flow reactor 2 with a mixing chamber 1 according to FIG. 1 is used, the length of the flow reactor being 60 cm (reaction length: 35 cm) and the inner diameter 16 mm. The flow reactor is made of quartz and is equipped with a heatable exterior jacket. Helium is used as carrier gas for the olefin. In the mixing chamber, 11.5 vol.-% of ozone is contacted with about 23 vol.-% $NO_2$ and 65.5 vol.-% oxygen. Each of the reactants is metered in gaseous form via mass flow control systems. No catalyst is used.

a) Reaction is performed at a pressure of 25 mbar and a temperature of 180° C.

b) Reaction is performed at a pressure of 10 mbar and a temperature of 140° C.

The results of Examples 1a and 1b are summarized in Table 1:

| Example | Pressure [mbar] | Temperature [° C.] | Residence time [s] | Propylene percentage [Vol.-%] | Propylene conversion [mole-%] | Selectivity [mole-%] |
|---|---|---|---|---|---|---|
| 1a | 25 | 180 | 0.25 | 1.9 | 49.6 | 68.9 |
| 1b | 10 | 140 | 0.28 | 4.0 | 52.2 | 81.3 |

In the table:
Residence time = residence time of the gas mixture in the reaction zone of the flow reactor
Propylene percentage in vol.-% = in the overall gas flow in the reaction zone
Propylene conversion [mole-%] = ratio of reacted moles of propylene and supplied moles of propylene × 100%
Selectivity [mole-%] = ratio of moles of propylene oxide formed and reacted moles of propylene × 100%

It was found that, without using a catalyst and in spite of mild reaction conditions, exceedingly short residence time in the reaction zone and thus, high throughput (space-time yield) is possible with the method according to the invention, the selectivity with respect to propylene oxide being very high.

Example 2

Oxidation of Trans-butylene to Form Cis/Trans-butylene Oxide (Mixture of Isomers)

Reactions are performed under the same conditions as in Example 1.

a) Reaction is performed at a pressure of 25 mbar and a temperature of 180° C.
b) Reaction is performed at a pressure of 25 mbar and a temperature of 230° C.

The results of Examples 2a and 2b are summarized in Table 2:

| Example | Pressure [mbar] | Temperature [° C.] | Residence time [s] | Butylene percentage [Vol.-%] | Butylene conversion [mole-%] | Selectivity [mole-%] |
|---|---|---|---|---|---|---|
| 2a | 25 | 180 | 0.25 | 1.45 | 84.3 | 80.0 |
| 2b | 25 | 230 | 0.23 | 1.45 | 53.1 | 96.9 |

The denotations in Table 2 correspond to those in Table 1.
Similarly, the results show that high conversion of the employed olefin and high throughput are achieved. The selectivity with respect to cis/trans-butylene oxide is nearly 100%.

Example 3

Oxidation of Isobutylene to Form Isobutylene Oxide

Reaction is performed under conditions as in Example 1, at a pressure of 10 mbar and a temperature of 230° C. The reaction length is 12 cm. The results are illustrated in Table 3.

| Example | Pressure [mbar] | Temperature [° C.] | Residence time [s] | Isobutylene percentage [Vol.-%] | Isobutylene conversion [mole-%] | Selectivity [mole-%] |
|---|---|---|---|---|---|---|
| 3 | 10 | 230 | 0.078 | 3.5 | 74.9 | 75.2 |

High conversion with respect to olefin employed and high selectivity are achieved.

What is claimed is:

1. A method of preparing an epoxide by oxidation of an olefin in a homogeneous gas-phase reaction, comprising mixing ozone and $NO_2$ and/or NO, feeding the resultant gas mixture into a flow reactor, and reacting the olefin in the flow reactor at a pressure of 0.1–1000 mbar and a temperature of 50–350° C.

2. A method according to claim 1, wherein the reaction is performed at a temperature of 100–300° C.

3. A method according to claim 1, wherein the reaction is performed at a pressure of 1–500 mbar.

4. A method according to claim 1, wherein the olefin is a monoolefin having 2 to 16 carbon atoms or a diolefin having 4 to 16 carbon atoms.

5. A method according to claim 1, wherein ozone and $NO_2$ and/or NO are mixed in a mixing chamber connected with the flow reactor.

6. A method according to claim 1, wherein ozone and $NO_2$ and/or NO are mixed with a carrier gas.

7. A method according to claim 1, wherein ozone and $NO_2$ are in an amount at a ratio smaller than 0.5.

8. A method according to claim 1, wherein ozone and $NO_2$ are in an amount at a ratio smaller than 1.5.

9. A method according to claim 1, wherein the flow reactor (2) has a heatable exterior jacket (3) and is connected with the flow reactor (2) to a mixing chamber (1), and optionally connected to a GC-MS analyzer and/or a gas flow cell with an FT-IR spectrometer.

10. A method according to claim 1, wherein the reaction is performed at a temperature of 140–240° C.

11. A method according to claim 1, wherein the reaction is performed at a pressure of 1–200 mbar.

12. A method according to claim 5, wherein the temperature in the mixing chamber is held at room temperature.

13. A method according to claim 1, wherein the reaction is performed without a catalyst.

14. A method according to claim 1, wherein the residence time in the reactor is 0.1 to 300 ms.

15. A method according to claim 6, wherein the carrier gas is oxygen, helium, argon or nitrogen, or a mixture of helium, argon or nitrogen with oxygen.

16. A method according to claim 1, wherein the ozone is supplied in an ozone/oxygen mixture.

17. A method according to claim 16, wherein the ozone/oxygen mixture contains 1–15 volume % ozone in oxygen.

18. A method according to claim 16, wherein the ozone/oxygen mixture contains 5–10 volume % ozone in oxygen.

19. A method according to claim 4, wherein the olefin is a monoolefin having 2 to 5 carbon atoms.

20. A method according to claim 4, wherein the olefin is a monoolefin having 4 carbon atoms or is propylene.

* * * * *